United States Patent [19]

Levy et al.

[11] Patent Number: 5,387,419
[45] Date of Patent: Feb. 7, 1995

[54] SYSTEM FOR CONTROLLED RELEASE OF ANTIARRHYTHMIC AGENTS

[75] Inventors: Robert J. Levy; Amnon Sintov, both of Ann Arbor, Mich.

[73] Assignee: The University of Michigan, Ann Arbor, Mich.

[21] Appl. No.: 37,810

[22] Filed: Mar. 26, 1993

Related U.S. Application Data

[60] Division of Ser. No. 647,931, Jan. 28, 1991, abandoned, which is a continuation-in-part of Ser. No. 173,534, Mar. 31, 1988, abandoned.

[51] Int. Cl.[6] .................................................. A61K 9/00
[52] U.S. Cl. ................................. 424/422; 424/423; 424/424; 424/425; 514/821; 604/891.1; 607/120; 607/129
[58] Field of Search ............... 424/423, 424, 425, 422; 514/821; 604/891.1; 607/129, 120

[56] References Cited

U.S. PATENT DOCUMENTS

| | | | |
|---|---|---|---|
| 4,309,996 | 1/1982 | Theeuwes | 424/424 |
| 4,344,431 | 8/1986 | Yolles | 424/425 |
| 4,615,697 | 10/1986 | Robinson | 424/424 |
| 4,627,836 | 12/1986 | MacGregor | 424/423 |
| 4,883,666 | 11/1989 | Sabel et al. | 424/423 |
| 5,028,430 | 7/1991 | Sanders et al. | 424/423 |
| 5,141,748 | 8/1992 | Rizzo | 424/423 |

*Primary Examiner*—Thurman K. Page
*Assistant Examiner*—Amy Hulina
*Attorney, Agent, or Firm*—Rohm & Monsanto

[57] ABSTRACT

A system for controlled release, site-specific delivery of therapeutic agents, particularly myocardial agents such as antiarrhythmic agents, comprises a biocompatible polymeric matrix with an incorporated therapeutic agent for direct placement at the epicardium. Advantageously, the dosage form can be fabricated in such a manner as to tailor the release characteristics as required by the nature of the physical condition desired to be treated. In a specific illustrative embodiment, lidocaine, an antiarrhythmic depressant, is incorporated in polyurethane by a unique method which permits drug-loading of the polymeric matrix from about 5% up to 40% by weight, with about 25% to 30% in a preferred embodiment. A novel $FeCl_3$ catalyst causes the polyurethane to polymerize despite the presence of drug in the polymeric matrix mixture.

1 Claim, 6 Drawing Sheets

SYSTEM FOR CONTROLLED RELEASE OF ANTIARRHYTHMIC AGENTS

GOVERNMENT RIGHTS

This invention was made with government support under Grant Nos. RO1-HL38118 and RO1-HL41663 awarded by the National Heart, Lung, and Blood Institute of the National Institutes of Health. The government has certain rights in the invention.

This is a division of U.S. Ser. No. 07/647,931 filed on Jan. 28, 1991, now abandoned, which was a continuation-in-part of U.S. Ser. No. 07/173,534 filed on Mar. 31, 1988, now abandoned.

BACKGROUND OF THE INVENTION (1) Field of the Invention

This invention relates to a controlled release dosage form for site-specific delivery of therapeutic agents and, more specifically, to a controlled release dosage form for direct transmyocardial delivery of antiarrhythmic agents and methods of making same.

(2) Background of the Prior Art

Life-threatening cardiac arrhythmias are a medical problem confronting millions of persons daily. Arrhythmias are the principal cause of death following myocardial infarction in hundreds of thousands of other persons. Furthermore, cardiac arrhythmias complicate one-third to one-half of the more than three hundred thousand open heart surgeries carried out annually in the United States.

Currently, the millions of persons suffering from cardiac rhythm abnormalities receive oral drug therapy. Examples of frequently prescribed oral antiarrhythmic therapeutic agents are Digitalis, Digitoxin and Procainamide. Other antiarrhythmic agents, such as lidocaine or amiodarone are given intravenously. Conventional drug therapy is often ineffective in either preventing or treating life-threatening ventricular arrhythmias due to inadequate drug concentrations where and/or when needed and adverse side effects of the drugs.

In addition to drug therapy, over one hundred thousand patients per year receive intracardiac electronic pacemakers for severe cardiac rhythm disturbances. However, there are significant problems created with surgical implantation and subsequent maintenance of electronic pacemakers. Recently, ablative surgical and catheterization techniques have been developed to destroy irritable myocardial tissue; but this has not been particularly effective. Accordingly, drug therapy, pacemaker implantation, and surgery are at best only partially effective for preventing and/or suppressing cardiac arrhythmias.

Implantable controlled release drug delivery systems have been investigated in a number of situations in order to achieve site-specific administration and/or prolonged delivery of a therapeutic agent into a particular body component at an effective, but minimal, dosage level in order to reduce the risk of toxic effects of the therapeutic agent. An example of such a system is an implantable infusion pump. Implantable drug delivery systems formulated from polymeric matrices have been developed for, inter alia, preventing infections in indwelling devices, such as urinary catheters, by incorporation of antibiotic agents.

The common practice in the prior art, however, is to bond the antibiotic or other drug to a coating on, for example, Dacron polyester or polytetrafluoroethylene (Teflon) materials. Known coatings include gelatin, albumin, graphite-benzalkonium, and cationic surfactants such as tridodecylmethylammonium chloride. In the case of antibiotics, the coatings present a cationic surface which bonds to the anionic antibacterial agent. The antibiotic, however, is rapidly dissipated in the body fluids although a certain amount of antibiotic does remain in the coating until the coating dissipates from the substrate material. Adverse effects, such as toxicity and thrombogenesis, are possible with the use of coatings.

Sustained site-specific cardiac drug delivery has been developed to prevent bacterial endocarditis, to prevent bioprosthetic heart valve calcification and to prevent fibrous tissue buildup. Thyroid and adrenal medulla myocardial autografts were investigated as "endocrinologic cardiac pacemakers." Drug delivery of chronotropic agents has also been accomplished by myocardial implants of silastic reservoirs containing a variety of compounds, including digoxin, isoproterenol, and thyroid hormone, all of which can effectively accelerate cardiac rate when delivered directly into the myocardium.

While these methods have been employed to stimulate and control cardiac rate by transmyocardial drug administration, there have been no examples in the prior art of treatment of ventricular arrhythmias by transmyocardial administration of antiarrhythmic agents.

Moreover, none of the above-described polymeric devices can be fabricated so as to have a particular dosage release characteristic. There are obvious advantages to rapid release of the antiarrhythmic agent immediately post-implantation, followed by slower, sustained release, in the treatment of certain conditions, such as acute arrhythmias.

It is, therefore, an object of the invention to provide biological or synthetic polymeric materials which are compatible with body tissues and which incorporate therapeutic agents, such as antiarrhythmic agents, for the treatment of cardiac rhythm disturbances.

It is a further object of the invention to provide a biocompatible polymeric matrix with incorporated antiarrhythmic agent which can be applied directly to the heart muscle via the epicardium, endocardium, or pericardium.

It is another object of the invention to provide a biocompatible polymeric matrix which incorporates a relatively high concentration of antiarrhythmic agent for site-specific delivery.

It is also an object of the invention to provide a biocompatible polymeric matrix with incorporated antiarrhythmic agent for site-specific delivery of an antiarrhythmic agent such that efficacious results are achieved at body concentrations which are lower than the required plasma level for effectiveness of oral or intravenous administration of such agent.

It is yet another object of the invention to provide a biocompatible polymeric matrix with incorporated antiarrhythmic agent for implantation in, or prolonged contact with, a human or animal body, which has the capability of supplying a high concentration of antiarrhythmic agent directly to the heart muscle, particularly during a critical phase, and of slowly releasing antiarrhythmic agent during an extended period of time thereafter.

It is an additional object of the invention to provide a technique for fabricating a biocompatible polymeric matrix with incorporated antiarrhythmic agent wherein the release characteristics of the antiarrhythmic agent can be selectably varied.

It is additionally an object of this invention to provide a biocompatible polymeric matrix with incorporated antiarrhythmic agent which eliminates or minimizes the side effects of antiarrhythmic agents yet optimizes the beneficial effects of these agents.

It is yet a further object of this invention to provide a more effective method of treatment of arrhythmia than current techniques such as oral or intravenous drug administration, cardiac pacemaker implantation, or surgical removal or destruction of irritable heart tissue.

SUMMARY OF THE INVENTION

The foregoing and other objects, features and advantages are achieved by this invention which provides a controlled release dosage form for delivery of antiarrhythmic agents comprising a biocompatible polymeric matrix material having incorporated therein a therapeutically effective amount of at least one antiarrhythmic agent. In preferred embodiments, the biocompatible polymeric material is a synthetic, nonbiodegradable polymer such as polyurethane, polydimethylsiloxane, ethylene vinyl acetate, polymethyl methacrylate, polyamide, polycarbonate, polyester, polyethylene, polypropylene, polystyrene, polyvinyl chloride, polytetrafluoroethylene, or cellulose acetate. In alternative embodiments, the biocompatible polymeric material is a biodegradable polymeric material such as collagen, polylactic-polyglycolic acid, or polyanhydride.

The incorporated antiarrhythmic agent may be either a cardiac stimulant, such as isoproterenol, dopamine, or norepinephrine or a cardiac suppressant, such as lidocaine.

A method of treating cardiac rhythm disturbances in living beings comprises direct controlled release delivery of an antiarrhythmic agent to the epicardium by application of an implantable device comprising a polymeric matrix incorporating the desired antiarrhythmic agent. The implantable device may be in any form which may be attached to the heart muscle in some manner such as a patch of film, coated wires, anchorable catheter tip, etc.

In a process aspect of the invention, a method of preparing a controlled release dosage form for the delivery of antiarrhythmic agents comprises the steps of:

(a) forming a polymeric substrate mixture by mixing a predetermined amount of a therapeutic agent, illustratively an antiarrhythmic agent, with a predetermined amount of polymeric precursor material;

(b) forming the polymeric substrate mixture in the desired configuration; and (c) curing the polymeric substrate mixture.

in an alternative embodiment, the polymeric substrate mixture can be formed by dissolving a fully polymerized polymeric material in an organic solvent in which the therapeutic agent is likewise soluble.

A catalytic agent can be employed to cure the polymeric substrate mixture and/or to aid in incorporation of therapeutic agent in the polymeric matrix. Advantageously, therapeutic agent can be incorporated in the polymeric matrix by any of the aforementioned techniques in about 5% to 40% by weight.

In one embodiment, the step of forming the polymeric material into the desired configuration comprises casting the polymeric mixture into a film. Usable film thicknesses may illustratively range from about 20 μm to 1 cm, with a typical thickness being on the order of 200 mm. In another advantageous embodiment, the polymeric mixture is molded into the desired substrate shape. Certain drug release characteristics can be achieved by molding under compression, illustratively in the range of about 8–10 tons p.s.i.

The dosage release characteristics may be tailored specifically by the process parameters. Rapid release characteristics in the initial stages following implantation of the controlled release dosage form in the epicardium of a patient followed by slow release over an extended period of time can be achieved by adding the following step to the above-described process: permitting the mixture to react to approximately the point in time where long chain polymerization is complete and crosslinking is about to occur and then briefly stirring the mixture to facilitate additional cross-linking.

In a specific advantageous embodiment of the invention, a lidocaine-polyurethane matrix for controlled release of the lidocaine is formed by the following process:

(a) forming a mixture of about 0.5 to 4 parts by weight lidocaine hydrochloride (a water soluble salt of the antiarrhythmic agent); 10 parts by weight polyurethane prepolymer, in a specific embodiment, said polyurethane prepolymer comprising about 0.21 parts diisocyanate monomer and about 0.79 parts polyether monomer; and a catalytic agent, specifically about 0.1 μM–1.0 μM $FeCl_3$/g polyether monomer;

(b) forming the mixture into a desired shape; and (c) curing the formed mixture at a relatively low temperature in the range of 50° C. to 60° C. for a period of time ranging from about 24 hours to 3 days.

In particular, the $FeCl_3$ catalyst in the lidocaine/polyurethane system has enabled a viable product to be formed with drug loading up to 40% w/w. In a preferred embodiment, drug loading of approximately 28% w/w has been found to have an optimum effect in correcting cardiac arrhythmic disturbances.

BRIEF DESCRIPTION OF THE DRAWING

These and other objects, features and advantages will be better appreciated from consideration of the following detailed description read in conjunction with the accompanying drawings, wherein.

DETAILED DESCRIPTION OF THE INVENTION

Figure 1:
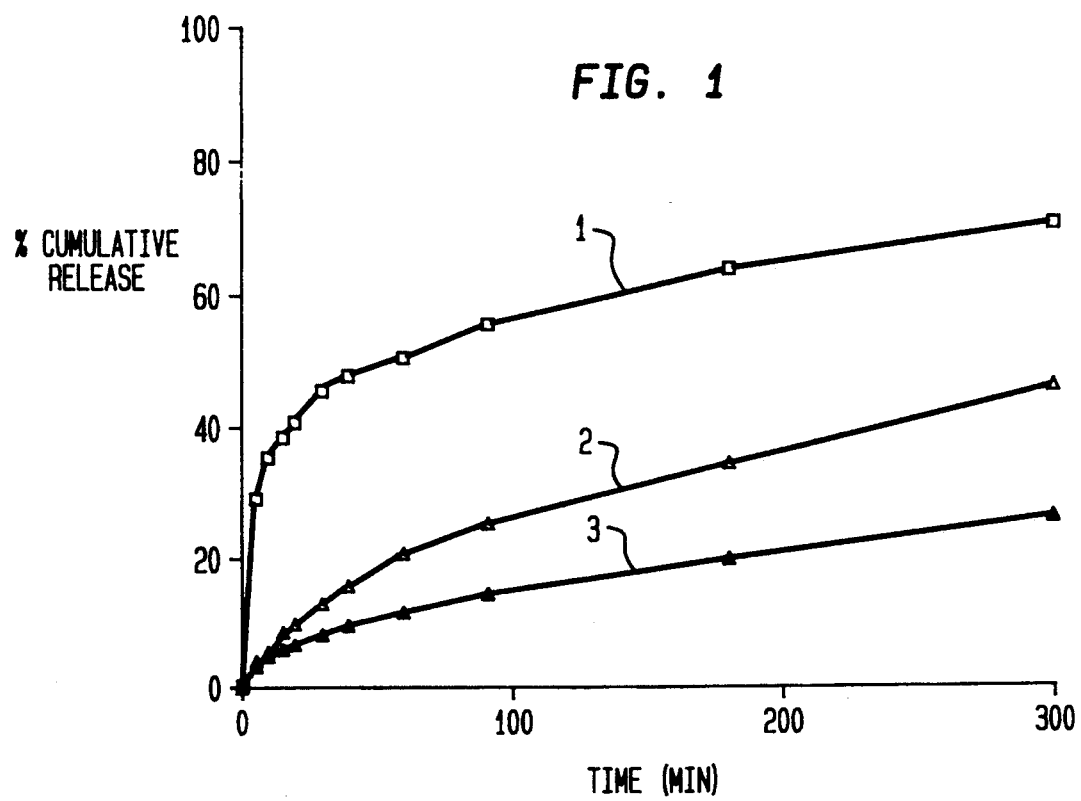
FIG. 1 is a graphical representation of the short term release characteristics of lidocaine-polyurethane matrices fabricated in accordance with the invention and expressed as % cumulative release versus time in minutes.

A novel controlled release dosage form is described hereinbelow for the therapy of cardiac arrhythmias wherein a substrate comprising a polymeric matrix incorporating at least one therapeutic agent is directly placed in contact with the heart muscle. The therapeutic agent then elutes, or diffuses, directly into the site where it is needed resulting in a rapid conversion from tachycardia to normal sinus rhythms. Direct contact of the dosage form with the heart muscle, either at the epicardium or the endocardium, or in some instances through the pericardium, is herein termed "transmyocardial delivery." A specific advantage of the novel dosage form is that transmyocardial delivery permits a lower dosage of antiarrhythmic agent to be used for localized, or regional, treatment, thereby mitigating the usual adverse side effects of such drugs when administered systemically in doses sufficient to be efficacious.

The polymeric matrix material is illustratively synthetic, such as polyurethane or dimethylpolysiloxane (Silastic). The synthetic polymeric matrix material is preferably flexible, elastomeric, and of great tensile strength so that the resulting controlled release dosage form for transmyocardial delivery will be able to withstand the intense mechanical activity of the heart. In this regard, polyurethane and dimethylpolysiloxane are ideal. In particular embodiments, where rapid release of antiarrhythmic agent would be desirable, such as to convert life-threatening arrhythmias to normal sinus rhythm as quickly as possible, hydrophilic polymers, such as polyurethane, are preferred.

Other examples include, without limitation, any biocompatible polymer, whether hydrophilic or hydrophobic, such as ethylene vinyl acetate, polymethyl methacrylate, polyamide, polycarbonate, polyester, polyethylene, polypropylene, polystyrene, polyvinyl chloride, polytetrafluoroethylene, or cellulose acetate. In an alternative illustrative embodiment, a biologically derived polymer, such as protein collagen, polylactic-polyglycolic acid, or polyanhydride, is a suitable polymeric matrix material.

For certain situations, such as short term arrhythmias associated with cardiac surgeries, biologically degradable polymeric matrices are advantageous since they can be resorbed by the body after a period of sustained drug delivery. On the other hand, for chronic recurring arrhythmias, nondegradable and/or potentially refillable or renewable, systems, such as a hollow polymeric reservoir, might be more appropriate.

Specific examples of two therapeutic agents, or drugs, which are currently in widespread usage for cardiac rhythmic disturbances and which are well-suited for inclusion in the controlled release dosage form of this invention are lidocaine and amiodarone. Lidocaine is a highly effective antiarrhythmic which is typically administered intravenously, and then only for a limited time due to the adverse side effects produced by this agent. Amiodarone can be given orally, but causes severe side effects in over 70% of the patients receiving it. Controlled release dosage forms of the present invention have been formulated to incorporate antiarrhythmic agents from the four generally recognized classes of antiarrhythmic agents (Vaughan-Williams classification). Some examples are given below in tabular form:

Type 1—Sodium Channel Blockers
  lidocaine
  procainamide
  encainide
  flecanide
Type 2—Beta Adrenergic Blockers
  propranolol
Type 3—Prolongers of the Action Potential Duration
  amiodarone
Type 4—Calcium Channel Blockers
  verapamil
  diltiazem
  nickel chloride Lidocaine, for example, is a cardiac depressant. Cardiac stimulants, such as isoproterenol, dopamine, and norepinephrine, can also be incorporated into polymeric matrices in accordance with the principles of this invention and, in some instances, may be used to treat heart failure. An exemplary combination of more than one myocardial agent is the digoxin/quinidine system used to treat atrial fibrillation.

It is to be understood, however, that any antiarrhythmic agent, or combination of antiarrhythmic agents or other drugs which are suitable for co-administration with antiarrhythmic agents, is within the contemplation of the invention. Therefore, the term "antiarrhythmic agent" as used herein means any agent or combination of agents that can be used to treat, or control, cardiac arrhythmias whose mechanism of action conforms to one or more of the four Vaughan-Williams classifications.

The antiarrhythmic agents are preferably provided in a water soluble form, such as the hydrochloride salt of lidocaine, to facilitate elution from the polymeric matrix material in the presence of body fluids.

The controlled release dosage forms may be placed directly on the heart muscle during open heart surgery, by cardiac catheter with a detachable tip, or by pericardiocentesis. Three illustrative substrate configurations for cardiac applications include an epicardial design for direct attachment to the surface of the heart which could be in the form of a polymeric film/patch (see FIG. 7), polymer-coated wires, or rigid screw-threaded molded polymeric structures. For intravascular placement via a cardiac catheter, a detachable screw-threaded catheter tip, or an expandable (umbrella) system with anchoring prongs are among the possible configurations which can be devised by one of ordinary skill in the art. Other configurations can be devised for intramyocardial placement via a stab wound with a sharp trochar. Techniques, such as film casting and compression molding, are applicable for fabricating the specific substrate configuration of the antiarrhythmic agent/polymeric matrix controlled release dosage form.

The configuration chosen would depend upon the type of arrhythmia condition being treated. A dosage form in the shape of a patch might advantageously be placed epicardially during open-heart surgery to avoid post-operative arrhythmia. A dosage form in the shape of a detachable screw-threaded catheter tip might be utilized to provide prophylaxis against cardiac arrhythmias following myocardial infarction. Moreover, as those of skill in the art are aware, certain antiarrhythmic agents are more suitable for chronic arrhythmias, for example, than acute arrhythmias, and therefore agents such as procainamide or sotalol would be a drug of choice for incorporation into a controlled release dosage form for application in a chronic arrythmia situation.

The dosage form may be a monolithic drug/polymer matrix, such as a film or implantable device, from which diffusion-mediated release occurs. In an alternative embodiment, a reservoir-type drug delivery system can be devised. Illustratively, the polymeric matrix material would be configured to form a hollow core reservoir with an access for refilling.

The novel dosage form would either replace or provide an important adjunct to existing oral or intravenous antiarrhythmic therapy. In addition, the dosage form could be used as part of procedures such as coronary arteriography, angioplasty, routine cardiac surgeries, catheterization and clinical electrophysiology studies. Moreover, inclusion of a dosage form such as described herein would provide additional drug therapy subsequent to pacemaker implantation.

There are various techniques for incorporating the therapeutic agent into the polymeric material matrix of the controlled release dosage form of the instant invention. General illustrative techniques include the following:

1. The therapeutic agent can be combined with the polymeric precursors so that the agent is incorporated as an element of the polymeric mixture prior to solid phase polymerization. Examples 1 and 2 herein are illustrative of this technique.

2. Polymerized matrix material is dissolved in an organic solvent. The therapeutic agent should also be soluble in the same organic solvent so that the therapeutic agent can be added directly to the dissolved polymer matrix material in the desired weight ratio. The mixture is then poured (solvent cast) into a mold, or cast as a film, and the solvent is permitted to evaporate. Examples 3 and 4, for example, are illustrative of this technique.

3. Fully polymerized matrix material can be milled, or mixed, with the therapeutic agent to form a blend which is then polymerized by the addition of a catalyst. Examples 5 and 6 herein are illustrative of this technique.

An advantageous feature of this invention is that drug release rate and duration can be regulated by process parameters. The duration can be varied from minutes to years, depending upon the formulation conditions of the polymeric matrix. The parameters which may be varied to control release rates include particle size of the therapeutic agent, disruption of the polymerization process with stirring, compression molding, and temperature of polymerization. The specific examples described hereinbelow illustrate the effects of some of these parameter variations. The results are graphically depicted in FIGS. 1–6.

Release characteristics of the drug-polymer combination can also be made responsive to feedback signals. An electrically responsive acrylamide polymer, for example, could be made to provide more drug when arrhythmia is detected and then to down-regulate when the abnormal rhythm has ceased.

Given below are several specific illustrative embodiments of biocompatible controlled release dosage forms in accordance with the invention and methods of making same. Also included are experimental results showing the efficacy and advantageous features of the dosage form under in vitro and in vivo conditions. Although Examples 1–5 are primarily directed to the preparation of polymeric matrices incorporating the antiarrhythmic agent lidocaine, the techniques described herein are applicable to the creation of a wide variety of other drug/polymer combinations and devices formed thereof. Additional examples (Examples 6 to 13) demonstrate that controlled release dosage forms in accordance with the principles of the invention have been fabricated to incorporate antiarrhythmic agents from all four classes of antiarrhythmic agents.

EXAMPLE 1

Lidocaine-polyurethane matrices were prepared by mixing about one to four parts of lidocaine hydrochloride (particle size 75–150 $\mu$m) with ten parts of Tecoflex 2-80A (a polyurethane prepolymer made by Thermedic Inc., Woburn, Mass.) comprising 0.21 parts of diisocyanate monomer and 0.79 parts of polyether monomer.

In the lidocaine/polyurethane example, prepolymerized polyurethane components will not react to form polymer in the presence of more than about 20% by weight of the antiarrhythmic agent. However, a $FeCl_3$ catalyst and slow curing at low temperatures will result in the formation of a stable polymer. In general, 0.1 $\mu$M to 1.0 $\mu$M $FeCl_3$ per g of polyether monomer is effective to provide a viable polymeric structure with up to 40% w/w drug loading. Advantageously, the resultant antiarrhythmic agent-polymer matrix will release antiarrhythmic agent with an accelerated early rate followed by a sustained, slower diffusion-controlled rate. The accelerated early rate is particularly advantageous in the treatment of acute arrhythmic disturbances.

In the specific illustrative embodiment of Example 1, 0.74 $\mu$M $FeCl_3$ per gram of polyether monomer was added as a catalyst. The mixture was then cast as a film of approximately 200 $\mu$m thickness and cured for 48 hours at 55° C. Of course, film thicknesses can vary, as a practical matter such thicknesses range from about 20 μm to 1 cm. Temperature and time ranges for polymerization can also range, respectively, from about 50° C. to 60° and from about 24 hours to 3 days.

a) In Vitro Experiments:

cumulative drug delivery in vitro of 28% w/w loaded lidocaine-polyurethane matrices, fabricated by the technique of Example 1, was monitored spectrophotometrically by absorbance at 260 nm. Samples of a perfect sink buffer solution were taken over time and the data was expressed as the means of duplicate measurements. The perfect sink buffer solution comprised 0.54M aqueous $K_2PO_4$ at a pH of 7.4 and temperature of 37° C.

Figure 2:
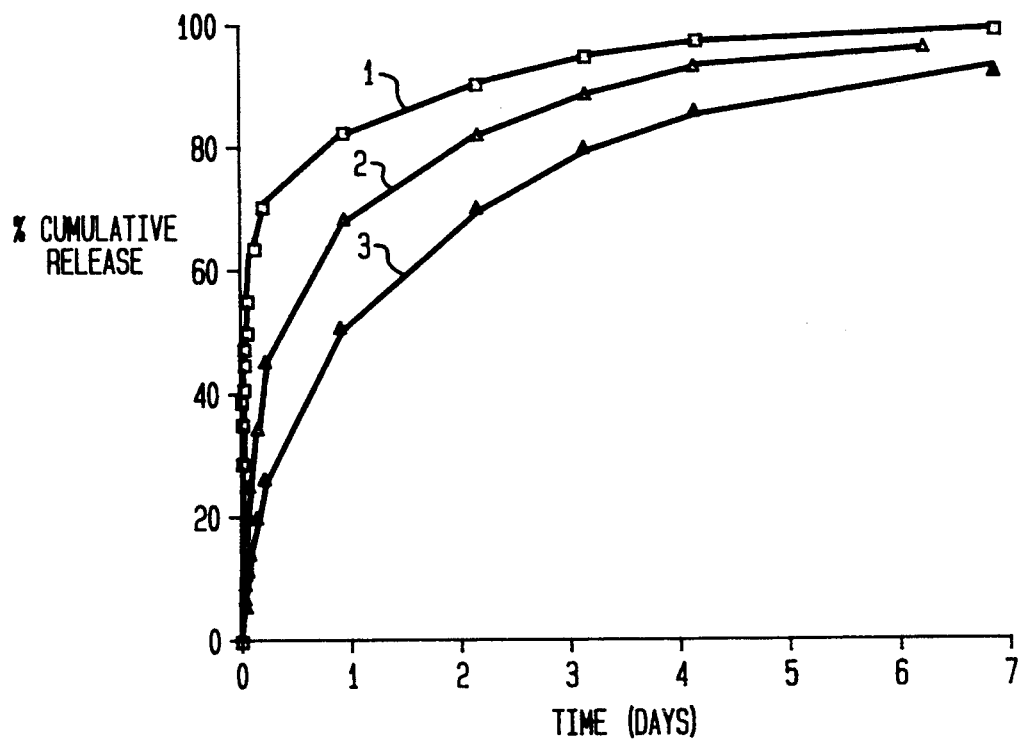
FIG. 2 is a graphical representation of longer term release characteristics of lidocaine-polyurethane matrices fabricated in accordance with the invention and expressed as % cumulative release versus time in days.

FIGS. 1 and 2 show the results of certain process variations to the method of Example 1 which affect the release of lidocaine. These process variations are (1) polymerization at 55° C. as described in Example 1; (2) an additional step of stirring the polymerization mixture after about 2 hours (post-long chain polymerization and pre-crosslinking) of reaction time; and (3) polymerization at room temperature. Referring specifically to FIG. 1, the short term release characteristics are graphically shown as a plot of % cumulative release versus time in minutes. Line 1 represents the release characteristics of the matrix formed in accordance with the process described in Example 1 (process variation (1) above); line 2 represents process variation (2) above; and line 3 represents process variation (3) above.

FIG. 2 is a graphical representation of long term release characteristics shown as a plot of % cumulative release versus time in days. Lines 1 through 3 represent the release characteristics of the matrices formed in accordance with processes (1) through (3), respectively.

The in vitro results show that variations in process parameters do affect the drug release characteristics of the drug/polymer matrix. In the polyurethane system of Example 1, the use of a higher molecular weight polyol in the polymer segments resulted in a more hydrophobic product, and hence a product capable of greater retention of the drug over time.

Figure 3:
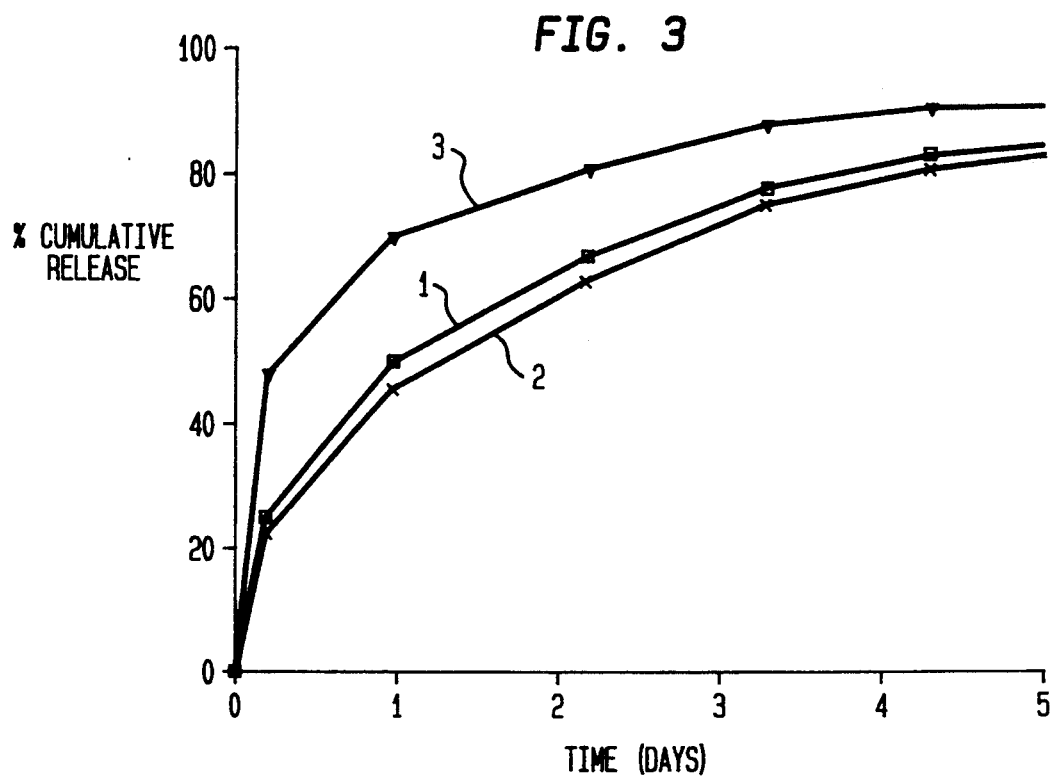
FIG. 3 is a graphical representation of long term release characteristics of lidocaine-polyurethane matrices fabricated in accordance with the invention and having varying drug loading ratios (wt. lidocaine: wt. polymer precursor) expressed as % cumulative release versus time in days.

In other experiments, the effect of various drug loading ratios was examined in vitro. Reference to FIG. 3 shows a graphical representation of long term release characteristics of lidocaine/polyurethane matrices having varying weight ratios of lidocaine to polyurethane. The data was obtained by spectrophotometric absorbance measurements and is expressed as % cumulative release versus time in days. The particular ratios examined were 2:10, 3:10, and 4:10 which are represented on FIG. 3 as lines 1, 2, and 3, respectively. The release rate profiles consisted of higher initial rates than the longer term diffusion-controlled rates. Moreover, as drug concentration was increased, initial rates increased while the diffusion-controlled rates remained about the same.

EXAMPLE 2

A lidocaine-polyurethane matrix combination was prepared in accordance with the method of Example 1. However, after a period of about 2 hours, when long chain polymerization was essentially completed, but prior to crosslinking, the reaction mixture was stirred for a short period of time, in this specific example, for 5 minutes.

Figure 4:
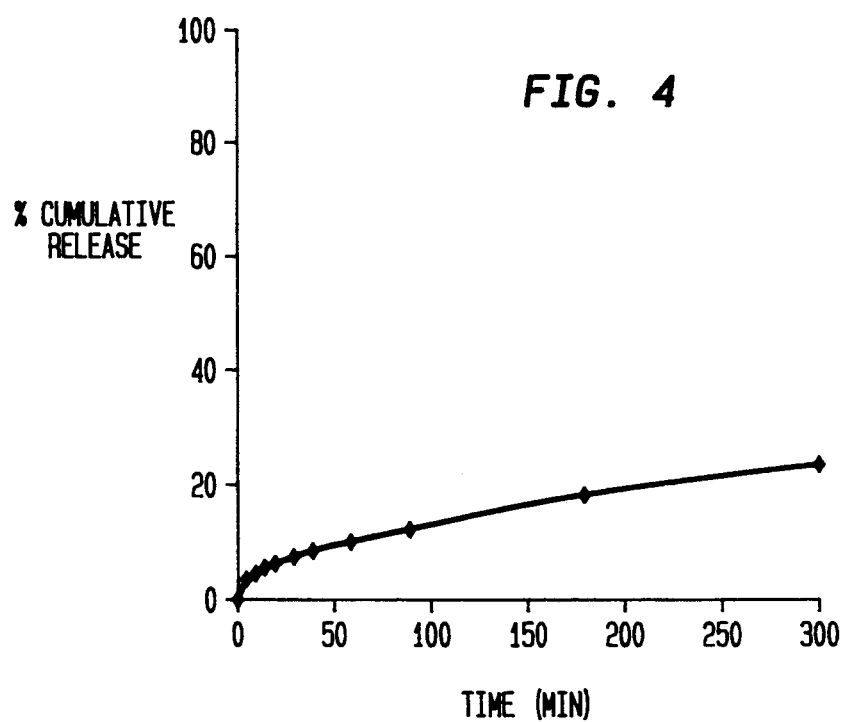
FIG. 4 is a graphical representation of short term release characteristics of a lidocaine-polyurethane matrix fabricated in accordance with an alternative embodiment of the invention wherein the matrix mixture was subjected to compression molding expressed as % cumulative release versus time in minutes.
Figure 5:
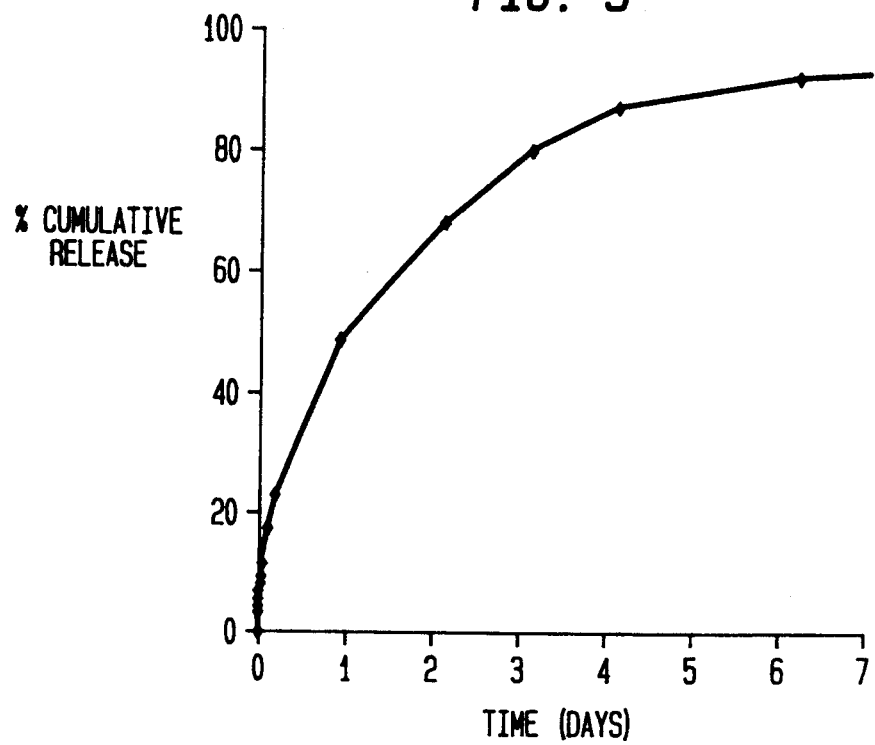
FIG. 5 is a graphical representation of longer term release characteristics of a lidocaine-polyurethane matrix fabricated in accordance with an alternative embodiment of the invention wherein the matrix mixture was subjected to compression molding expressed as % cumulative release versus time in days.

This mixture was then compression molded under 8-10 tons p.s.i. The long and short term release characteristics in vitro of the resultant dosage form are shown in FIGS. 4 and 5 as a function of % cumulative release versus minutes and days, respectively. Compression molding markedly decreases the release rate.

EXAMPLE 3

A lidocaine-polyurethane matrix combination was prepared by a solvent casting technique. Fully polymerized polyurethane was dissolved in an organic solvent, such as dimethylacetamide (DMAC) to form a clear, liquid solution. The desired amount of lidocaine was added into this solution. The solution was then cast as films 2-4 mm in thickness.

Figure 6:
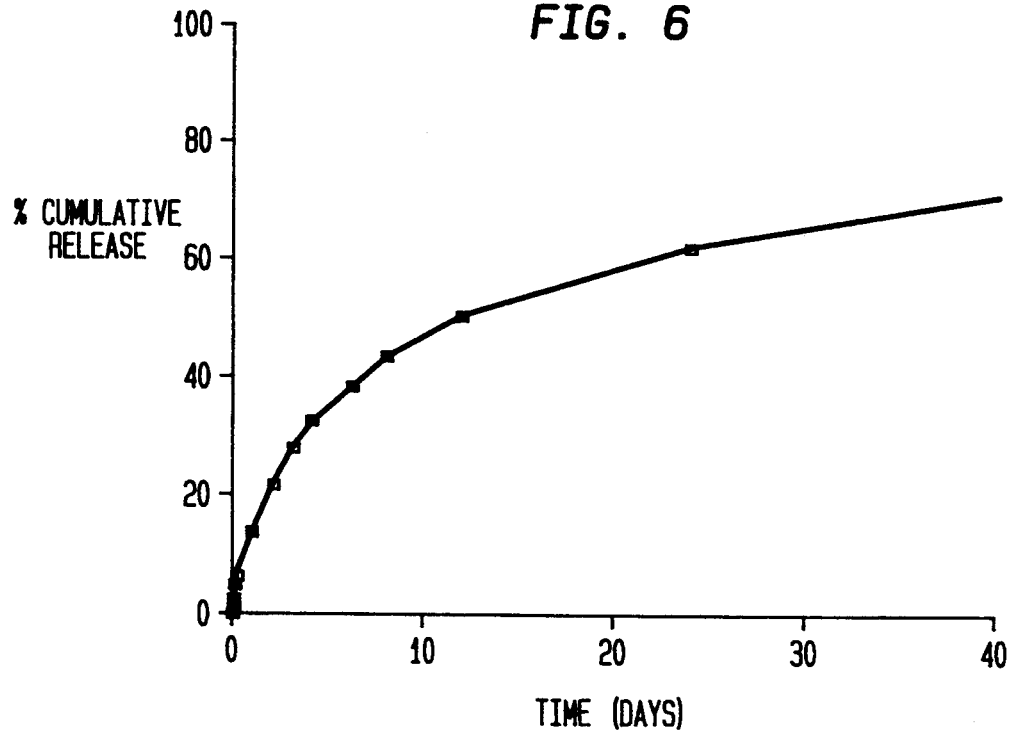
FIG. 6 is a graphical representation of long term release characteristics of a lidocaine-polyurethane matrix fabricated in accordance with an alternative embodiment of the invention wherein the matrix mixture was solvent cast from a solution of dimethylacetamide expressed as % cumulative release versus time in days.

FIG. 6 is a graphical illustration of the long term release characteristics for the solvent cast dosage form fabricated in accordance with this Example. This in vitro experiment was conducted at pH 7.4 in the same manner as described hereinabove with respect to Example 1. Comparing the results of FIG. 2 with FIG. 6, it is observed that the solvent casting technique results in a greater prolongation of sustained release of the therapeutic agent.

A polymeric matrix of the type described hereinabove was used to demonstrate the effective transmyocardial administration of lidocaine by direct placement of a patch of said matrix on the epicardial surface of a canine heart. The following experiment details the inhibition of ouabain-induced ventricular tachycardia with epimyocardial implants of the controlled release lidocaine-polyurethane matrix system fabricated in accordance with Example 1.

b) In Vivo Experiments:

Ventricular tachycardia was induced with ouabain administration in accordance with a method described in an article by Kniffen, et al., *Circulation*, Vol. 49, page 264, 1974. Ouabain is a cardiac glycoside which is used therapeutically for its rapid digitalizing effect. The experiment involved 14 male mongrel dogs weighing from 12-14 kg each. Ouabain obtained from Sigma Inc., St. Louis, Mo., was administered at an initial dose of 40 micrograms/kg at a rate of 40 micrograms/minute, and at subsequently halved dosages until sustained ventricular tachycardia was documented by electrocardiogram.

Figure 7:
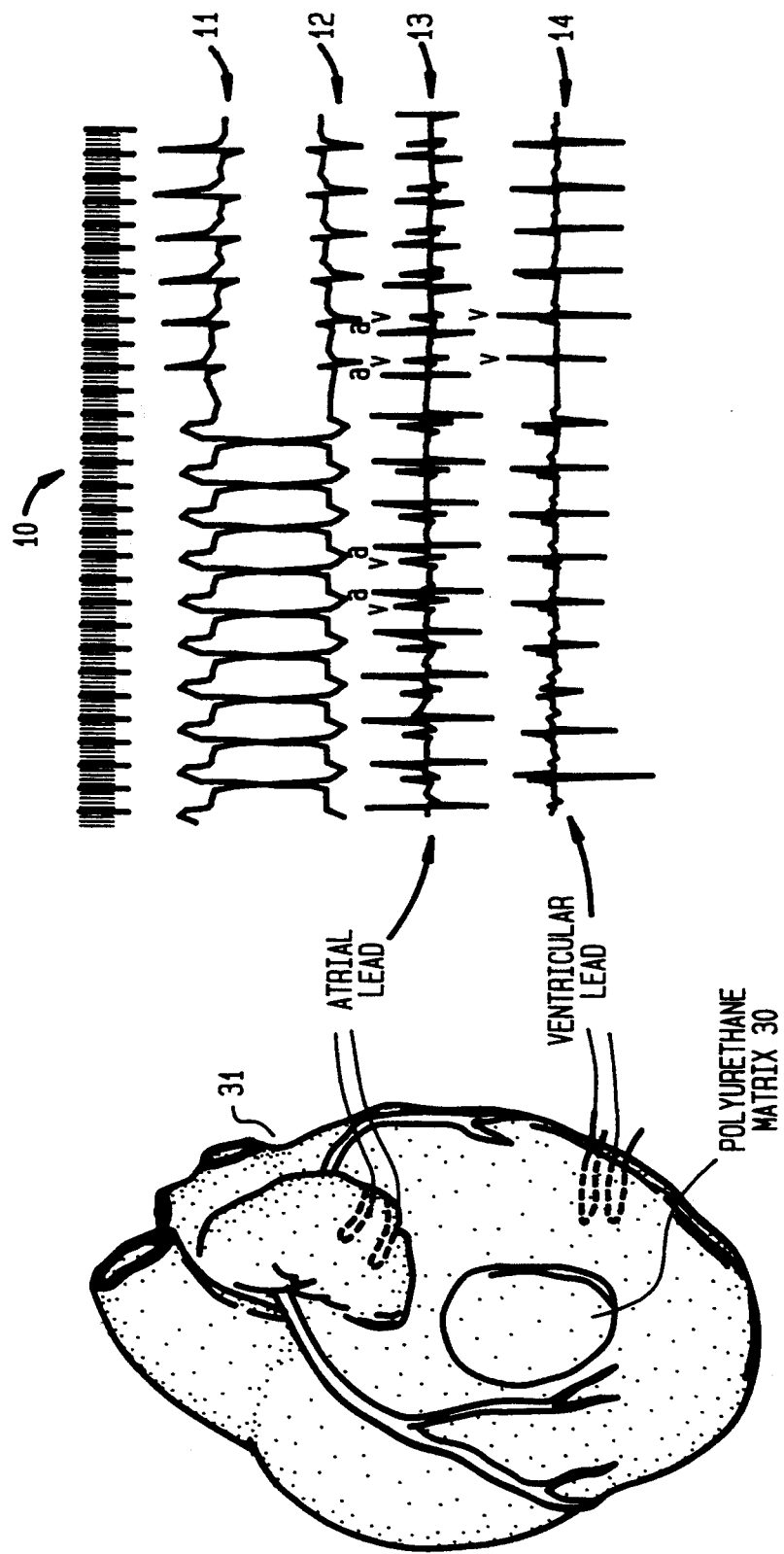
FIG. 7 is an illustrative electrocardiogram of a canine subjected to ouabain-induced tachycardia followed by direct application of a lidocaine-polyurethane patch fabricated in accordance with this invention to the epicardial left ventricular myocardium.

Each dog was subjected to a left thoracotomy in order to induce ventricular tachycardia with administered ouabain. Referring to FIG. 7, a polymeric patch 30 having dimensions of 3 cm×3 cm×0.2 cm was applied to the epicardial left ventricular myocardium of heart 31 about 1-2 cm to the left of the anterior descending coronary artery, about 1-2 cm below the circumflex coronary.

FIG. 7 is also illustrative of an electrocardiogram obtained as a result of this experiment. Electrocardiographic configuration was obtained with standard surface limb leads, as well as atrial and ventricular leads. Recordings from the limb leads are shown at 11 and 12 and atrial and ventricular deflections are 13 and 14, respectively. Conversion of ventricular tachycardia after placement of a lidocaine-polyurethane matrix to normal sinus rhythm is indicated by arrow 10. In each animal, the lidocaine-polyurethane matrix patch 30 was left in place on the left ventricular myocardium for the time needed to convert the ventricular tachycardia to normal sinus rhythm. When normal sinus rhythm reappeared, patch 30 was removed after one minute had elapsed, and the experiment was continued in order to detect the return of the induced arrhythmia. Some dogs had patches of polyurethane only as controls.

Ouabain-induced ventricular tachycardia in the dog was converted to normal sinus rhythm in all experimental animals studied via controlled release drug delivery of lidocaine from a polymeric matrix attached directly to the ventricular myocardium as shown in Table I wherein time is given in terms of mean ± standard error.

TABLE I

| Polymer Application | Number or Animals In Ventricular Tachycardia | | Time (min) |
|---|---|---|---|
| | Initial | Final | |
| Polyurethane | 4/4 | 4/4 | >60 |
| Lidocaine/Polyurethane | 6/6 | 0/6 | 1.5 ± 0.77 |
| Removal of Lidocaine/Polyurethane | 0/6 | 3/6 | 15.0 ± 25.0 |

The results given in Table I for the time range for return of ventricular tachycardia after removal of the lidocaine-polyurethane matrix is for three animals. The remaining three animals continued in normal sinus rhythm for greater than 60 minutes. In animals with the control patches, ventricular tachycardia continued for more than 60 minutes without the resumption of normal sinus rhythms. The lidocaine-polyurethane patch converted the ventricular tachycardia to normal sinus rhythm in 1.5±0.77 minutes.

Figure 8:
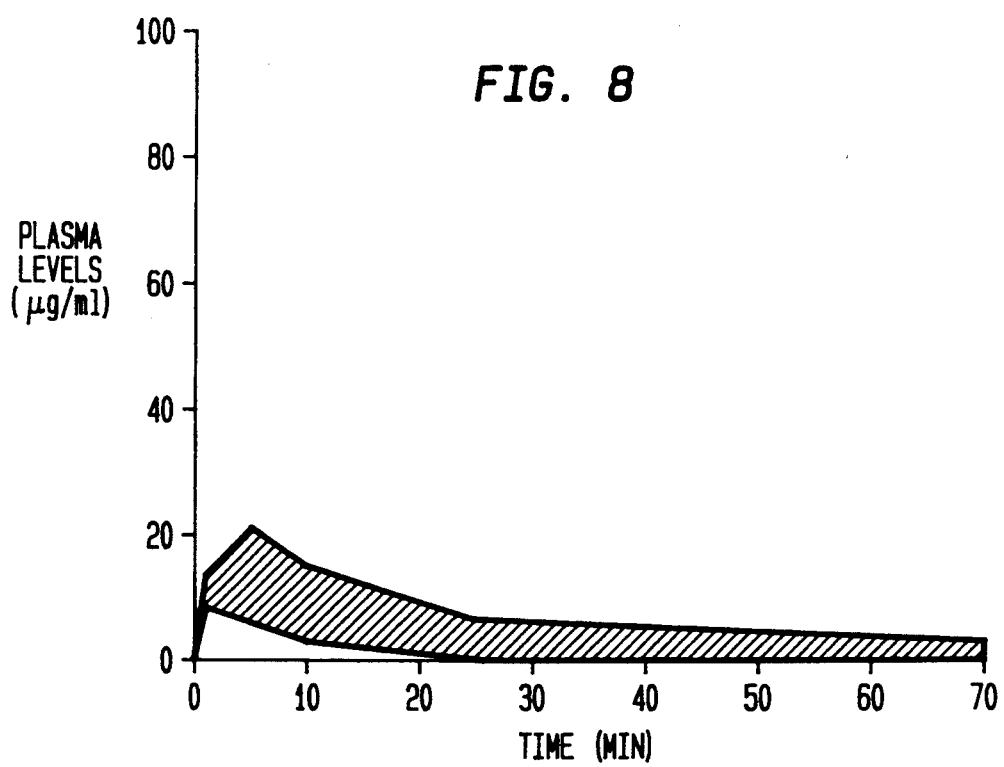
FIG. 8 is a graphical representation of blood plasma level of lidocaine in a canine subject with time for transmyocardial delivery via a lidocaine-polyurethane patch in accordance with this invention.
Figure 9:
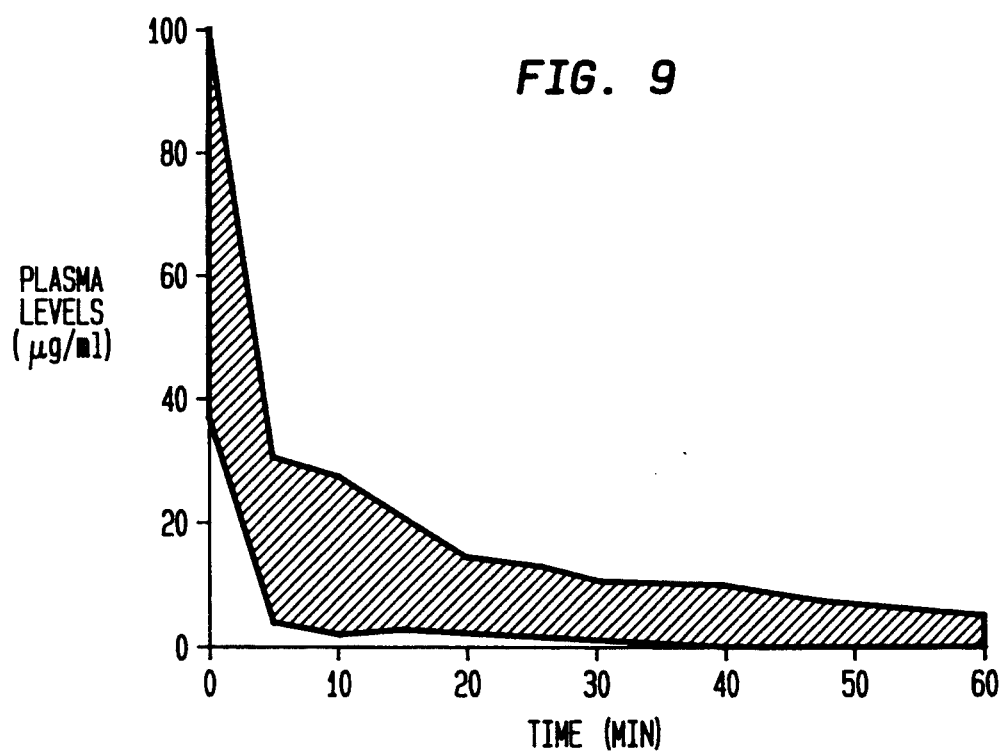
FIG. 9 is a graphical representation of blood plasma level of lidocaine in a canine subject with time for an intravenous bolus dose of lidocaine, comparable to the transmyocardial dose administered and shown in FIG. 8.

Dog studies analyzing blood plasma levels of lidocaine indicated that myocardial application of a lidocaine-polyurethane patch resulted in therapeutic effects as rapidly as lidocaine administered intravenously by bolus dose, but with comparatively lower plasma levels as determined by high performance liquid chromatography. Referring to FIG. 8, lidocaine plasma levels in the canine study are shown as the means of duplicate measurements for plasma levels in six dogs and their time-dependent decay after epicardial lidocaine-polyurethane therapy. In comparison, FIG. 9 shows plasma levels for 2 dogs following intravenous administration of 24 mg/kg and 45 mg/kg doses of lidocaine. The intravenous dosage levels were chosen to correspond to approximately the same dosage level as epicardial administration achieved by the polymeric patch as determined by sohxlet methanolic extraction of the residual drug remaining in the polymeric matrices after in vivo use, followed by subsequent high performance liquid chromatography utilizing a Waters Model 6000A system (Waters, Inc., Bedford, Mass.) with a prepacked C18 column (particle size 5 μm), Altex ultrasphere-ODS 25 cm×4.6 mm I.D. (Beckman Inc., San Ramon, Calif.) and an isocratic mobile phase of 0.1M sodium phosphate buffer at pH 3.0 with 0.7% v/v triethylamine-acetonitrile (50:50). Absorbance was monitored at 210 nm.

The above-described experimental results demonstrate that transmyocardial site-specific drug delivery is an effective route for the administration of antiarrhythmic therapy. The direct epicardial placement of lidocaine-polyurethane controlled release matrices resulted in the prompt conversion of induced arrhythmia to normal sinus rhythm in all experimental animals studied in about 1.5 minute, while controls had persistent ventricular tachycardia for more than 60 minutes. Site specific therapy was as rapid as intravenous administration, yet resulted in lower plasma lidocaine levels for comparable dosages.

In a study conducted on the transmyocardial delivery of lidocaine-loaded polyurethane patches attached to the epicardia of dogs, net doses of between 19 mg/kg and 45 mg/kg of lidocaine were delivered. However, the plasma levels of lidocaine were 8.75 to 25 μg/ml for the controlled release dosage form of the present invention as compared to 36.7 to 101.2 μg/ml following administration of a comparable dose intravenously. Thus, the direct myocardial placement of the dosage form described herein would mitigate adverse side effects of lidocaine, or any other antiarrhythmic agent administered in that manner.

EXAMPLE 4

Lidocaine has been incorporated into an ethylcellulose matrix by a solvent casting technique using various solvents, including chloroform, methylene chloride, and ethylacetate. The lidocaine loading ratio was 2:10.

EXAMPLE 5

Lidocaine in a silastic matrix was made by blending fully polymerized Silastic 382, a trademark of Dow-Corning, Midland, Mich., with lidocaine. In the instant case, 5% lidocaine by weight was added to the Silastic. This blend was polymerized by the addition of a stannous octanoate catalyst.

EXAMPLE 6

An isoproterenol-polydimethylsiloxane matrix dosage form has been fabricated and found to produce efficacious results. Pre-polymerized polydimethylsiloxane (PDMS) was milled together with powdered isoproterenol (5–20% by weight relative to the weight of PDMS) to form a blend. The blend was then catalyzed, either by heat or by addition of a chemical such as stannous octanoate or platinum oxide, and permitted to polymerize.

Controlled release matrices having antiarrhythmic agents from the four Vaughan-Williams classifications of antiarrhythmic agents have been formulated in various polymeric matrices. Specific illustrative examples are set forth hereinbelow. The Type 1 sodium channel blockers, such as lidocaine, procainamide, encainide, and flecanide, are represented in Examples 1–5 hereinabove.

EXAMPLE 7

A Type 2 (beta adrenergic blockers) antiarrhythmic agent, propranolol, has been incorporated into various polymeric matrix materials, particularly polyurethanes, such as Mitralthane MPU-5 (a polyurethane available from Symbion, Denver, Colo.) or biomer (a polyurethane available from Ethicon, Sommerville, N.J.), in amounts of up to 30% wt/wt. in accordance with the method of Example 3.

EXAMPLE 8

Type 3 antiarrhythmics, which prolong the action potential duration, are represented by amiodarone (available from Wyeth, Philadelphia, Pa.) in specific illustrative embodiments.

Amiodarone has been incorporated in a polyurethane matrix by the method of Example 3. More specifically, amiodarone was dissolved in dimethylacetamide to form a solution having a concentration of 100 mg/ml therapeutic agent. This solution was further dissolved in a 10% solution of polyurethane (Thyomer, Thermedics, Inc., Woburn, Mass.) with polyethyleneglycol (PEG 200, Dow, Midland, Mich.) as a 10% cocipient. This solution was solvent cast into a 0.2 mm film and used in the studies reported below in Table II. Polyethyleneglycol facilitates the release of the amiodarone from the polyurethane matrix.

EXAMPLE 9

Another Type 3 antiarrhythmic agent, d-sotalol (Bristol-Meyers Squibb, Wallingford, Conn.) was incorporated into polyurethane (Mitralthane MPU-5) in accordance with the procedure of Example 3 and used in the canine study reported hereinbelow in Table III.

EXAMPLE 10

Type 4 antiarrhythmic agents, or calcium channel blockers, including verapamil, diltiazem, and nickel chloride have been incorporated into various polymeric matrix materials, such as polyurethanes such as Mitralthane MPU-5, and silastics such as Q7-4850 in accordance with a solvent casting technique as described in Example 3.

EXAMPLE 11

Antiarrhythmic agents have been incorporated into exemplary biodegradable matrices such as a high molecular weight polyanhydride, polysebacic acid-carboxyphenoxy propane (Nova, Baltimore, Md.) and purified rat tail collagen. Films can be cast from the anhydride by dissolving it in methylene dichloride. The collagen may be cast from a solution in 0.1M acetic acid.

EXAMPLE 12

In Vivo Ventricular Pacing Studies

Ventricular tachycardia was induced and maintained by rapid ventricular pacing in an open-chest dog model using male mongrel dogs (10–15 kg). Three sets of bipolar epicardial electrodes were placed at 2 cm distances from the left ventricular apex toward the base of the heart. A Grass Model 8 stimulator (Grass Instruments, delivered continuous electrical stimulation as 2-msec square wave impulses with a 50-msec cycle length via a stimulus isolation unit (Bloom Associates, Reading, Pa.). The stimulus isolation unit also repeatedly monitored the pacing current thresholds. After induction of ventricular tachycardia, a controlled release dosage form of the present invention in the shape of a patch of the drug-loaded polymeric matrix material was placed adjacent to the stimulating electrode. The time required to convert the ventricular tachycardia to sinus rhythm was measured, as well as the time course of the quantitative change for sustaining the induction of ventricular tachycardia. The results are reported below in Table II. The effects of controlled release were monitored for up to 4 hours after conversion to normal sinus rhythm.

The lidocaine-Tecoflex patch was manufactured in accordance with Example 1 hereinabove. All other dosage forms were fabricated by dissolving the therapeutic agent in dimethylacetamide at a concentration of 100 mg/ml therapeutic agent. This solution was further dissolved in a 10% solution of a Thyomer polyurethane and solvent cast into a 0.2 mm films. Amiodarone matrices were cast with polyethyleneglycol as a 10% cocipient as described in Example 8. Controls comprised patches of each polymeric matrix material.

TABLE II

Transmyocardial Controlled-Release Conversion of Ventricular Tachycardia (VT) Induced by Rapid Ventricular Pacing

| Agent | No | Polymer Matrix | Drug Loading | Conversion (minutes) | Peak % Increase in VT Threshold |
|---|---|---|---|---|---|
| Lidocaine | 16 | Tecoflex | 28% | 0.86 ± 0.68 | 367.7 ± 183.1 |
| Procainamide | 7 | Thyomer | 30% | 4.05 ± 3.15 | 206.7 ± 172.6 |
| Amiodarone* | 3 | Thyomer | 30% | 5.90 ± 5.45 | 36.1 ± 12.7 |
| NiCl$_2$ | 4 | Thyomer | 50% | 2.08 ± 1.71 | 122.6 ± 101.3 |
| Control | 5 | Tecoflex | 0.0 | no effect | no effect |
| Control | 2 | Thyomer | 0.0 | no effect | no effect |
| Control | 1 | Thyomer* | 0.0 | no effect | no effect |

*with 10% polyethyleneglycol, 200; Data as mean ± standard error.

Referring to Table II, the site-specific application permitted the lidocaine-containing form to be effective at net dosages of only 0.1 mg/kg. Moreover, peripheral plasma levels of lidocaine were undetectable despite effectiveness in converting-tachycardia to normal sinus rhythm. Other studies revealed that lidocaine administered by this route created no other significant effects on normal cardiac function.

Procainamide was also effective in converting ventricular tachycardia in the ventricular pacing model.

Amiodarone is a highly effective antiarrhythmic agent which is frequently associated with severe side effects. It efficacy when utilized in the controlled release dosage form of the present invention demonstrates that the transmyocardial route of administration may be the safest and most effective manner of delivering this drug.

Nickel chloride is an example of a prototype drug system which would be difficult to administer systemically, but which has shown promise as an antiarrhythmic. However, the results of Table II show that nickel chloride is effective to convert tachycardia to normal sinus rhythm by direct epicardial application in the controlled release dosage form of the present invention.

Figure 10:
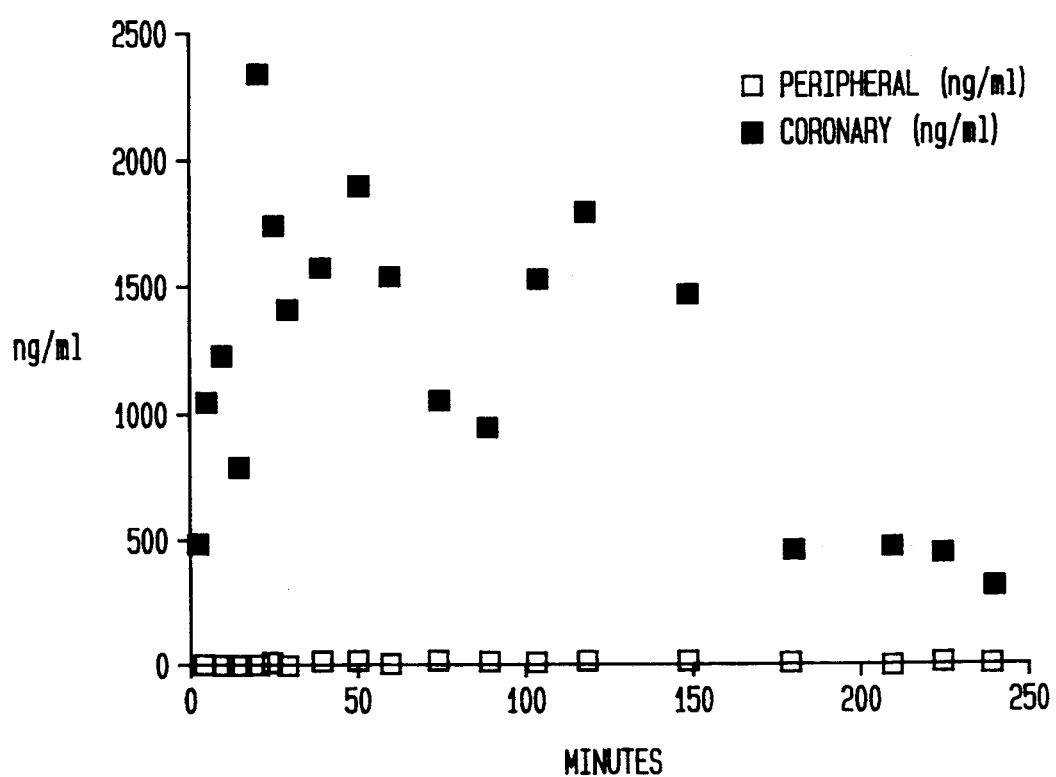
FIG. 10 is a graphic representation of the difference in coronary venous blood levels of antiarrhythmic agent versus systemic blood levels for transmyocardial delivery of lidocaine in a controlled release lidocaine-polyurethane matrices (28% w/w; 44 mg, 5 mm × 5 mm epicardial patches) of the present invention.

A pharmacokinetic study performed with controlled release the lidocaine-polyurethane matrices (28% w/w; 44 mg, 5 mm×5 mm epicardial patches) demonstrated the significance of site-specific application of the controlled release dosage of the instant invention. FIG. 10 is a graphic representation of the difference in coronary venous blood levels of antiarrhythmic agent versus systemic blood levels.

The lidocaine-polyurethane matrix was placed on the left ventricular epicardium of dog adjacent to the pacing-electrode. Lidocaine plasma levels were measured by a high performance liquid chromatographic assay in samples obtained over a 4 hour period of epicardial matrix application. Referring to FIG. 10, a total dose of 920 μg/kg was delivered. Regional coronary venous plasma levels of lidocaine were in the range of 0.8–2.3 μg/ml while simultaneously sampled peripheral blood levels were about 100fold lower, or 5.4–20.3 ng/ml).

EXAMPLE 13

In Vivo Ischemia-Induced Ventricular Tachycardia Studies

Controlled release dosage forms of the present invention have been successful in preventing ischemia-induced ventricular tachycardia in a canine model. Ventricular occlusions of the left anterior descending coronary artery of a dog were produced by exposing and isolating the artery in a dog under anesthesia. A snare with a sliding closure was placed around the artery. Ventricular tachycardia was produced by closing the snare for 10 minutes to shut off the blood supply to left ventricle. The snare was opened for an hour, and then the snare was closed for 10 minutes. This procedure can be repeated up six times and simulates a heart attack. Ventricular tachycardia (VT) was defined as the occurrence of 3 or more sequential ventricular premature beats. The efficacy of various controlled release dosage forms of the present invention were documented by continuous recording of the electrophysiologic data on a Hewlett Packard Physiologic Records, and an 8-channel analogue tape deck (Hewlett Packard, Philadelphia, Pa.). The results are shown in Table III.

TABLE III

| Antiarrhythmic Controlled Release Therapy: Results of Acute Ischemia-Ventricular Tachycardia (VT) Studies in Dogs | | | | | | | |
|---|---|---|---|---|---|---|---|
| Drug (per/minute) | Type* | Mechanism | Polymer | Loading | Dose (mg/kg/2hr) | N | VT |
| Lidocaine 0.6 ± 0.2 | 1 | Na Channel Blockade | Tecoflex | 28% | 0.23 | 5 | |
| Propranolol 1.22 ± .12 | 2 | Beta Blocker | MPU-5 | 30% | 0.14 | 6 | |
| D-Sotalol .046 ± .11 | 3 | Delayed Repolarization | MPU-5 | 30% | 0.20 | 9 | |
| Verapamil 0.10 ± .03 | 4 | Calcium Channel Blocker | MPU-5 | 30% | 0.30 | 11 | |
| No Therapy 1,10 ± 0.30 | — | — | Control | — | — | 9 | |

*Vaughan-Williams classification

Referring to Table III, the total dose over a 2 hour period (mg/kg/2 hr) for the various drug-loaded matrices was estimated from in vitro release data which has been found to correlate well with in vivo release rates. The data is expressed as the average for the number N of dogs per group. Episodes of VT were paced at one per minutes. Table III shows the number of VT episodes per minute following epicardial placement of the identified drug-loaded matrix. The Type 2 calcium channel blocker, verapamil, and the Type 3 agent, D-sotalol, were the most effective for arrhythmias due to acute myocardial ischemia. Interestingly, verapamil is contraindicated for arrhythmias when given systemically. However, Table III demonstrates the effectiveness of verapamil for transmyocardial delivery.

Although the invention has been described in terms of specific embodiments and applications, persons skilled in the art, in light of this teaching, can generate numerous and varied embodiments with these principles without departing from the spirit and scope of the claimed invention. Accordingly, it is to be understood that the descriptions in this disclosure are proffered to facilitate comprehension of the invention and should not be construed to limit the scope thereof.

What is claimed is:

1. A method of making a device for controlled release of an antiarrhythmic drug comprising:
   (a) forming a mixture of about 4 parts lidocaine hydrochloride; 10 parts polyurethane prepolymer, said polyurethane prepolymer comprising about 0.21 parts diisocyanate monomer and about 0.79 parts polyether monomer; and about 0.74 μM FeCl$_3$/g polyether monomer;
   (b) forming the mixture into a desired shape; and
   (c) curing the formed mixture at a temperature in the range of 50° C. to 60° C. for a period of time ranging from about 24 hours to 3 days.

* * * * *